United States Patent [19]

Abe et al.

[11] Patent Number: 5,389,601
[45] Date of Patent: Feb. 14, 1995

[54] 3-ALKOXY-N-CYCLOALKYLSULFONYALK-ANOIC AMIDE DERIVATIVE AND HERBICIDE USING THE SAME

[75] Inventors: Takaaki Abe; Yuji Akiyoshi; Hiroshi Shiraishi; Ikuo Shiraishi; Takashi Hayama, all of Ube, Japan

[73] Assignee: Ube Industries, Ltd., Yamaguchi, Japan

[21] Appl. No.: 93,859

[22] Filed: Jul. 20, 1993

[30] Foreign Application Priority Data

Jul. 21, 1992 [JP] Japan ................... 4-235071

[51] Int. Cl.$^6$ ............... C07D 239/60; A01N 43/54
[52] U.S. Cl. ..................... 504/243; 544/301
[58] Field of Search ................ 504/243; 544/301

[56] References Cited

FOREIGN PATENT DOCUMENTS

| | | |
|---|---|---|
| 347811 | 12/1989 | European Pat. Off. . |
| 400741 | 12/1990 | European Pat. Off. . |
| 409368 | 1/1991 | European Pat. Off. . |
| 411706 | 2/1991 | European Pat. Off. . |
| 481512 | 4/1992 | European Pat. Off. . |
| 517215 | 9/1992 | European Pat. Off. . |

*Primary Examiner*—John M. Ford
*Attorney, Agent, or Firm*—Finnegan, Henderson, Farabow, Garrett & Dunner

[57] ABSTRACT

Disclosed are a 3-alkoxy-N-cyclolalkylsulfonylalkanoic amide compound represented by the formula (I):

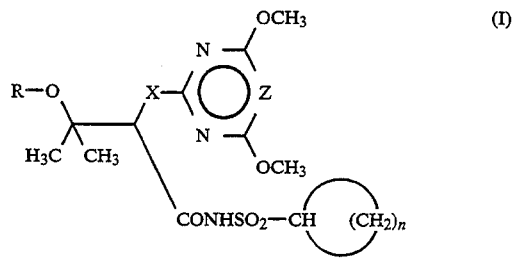

wherein R represents a lower alkyl group, a lower alkenyl group, a lower alkynyl group, a halo-lower alkyl group or a cyano-lower alkyl group; X represents an oxygen atom or a sulfur atom; Z represents a —CH= group or a nitrogen atom; and n represents an integer of 2 to 9, a process for preparing the same and a herbicide containing the same as an active ingredient(s).

8 Claims, No Drawings

3-ALKOXY-N-CYCLOALKYLSULFONYLALK-ANOIC AMIDE DERIVATIVE AND HERBICIDE USING THE SAME

BACKGROUND OF THE INVENTION

This invention relates to a herbicide containing a novel 3-alkoxy-N-cycloalkylsulfonylalkanoic amide derivative as an active ingredient.

Many herbicides have heretofore been developed for promoting labor-saving of farm practices and increase in productivity of crops. Conventional herbicides are, however, not sufficient in herbicidal effect and selectivity to crops such as cotton and soy bean, and also not sufficiently satisfactory in the point of safety to creatures. Thus, in order to solve these problems, development of a novel herbicide has been demanded. The present inventors have previously published a pyrimidine or triazine derivative in Japanese Provisional Patent Publications No. 360887/1992, No. 148242/1993 and No. 148245/1993 (all of which correspond to EP-A-0 517 215 and CN 107651A which are published after priority date of this application) but a 3-alkoxy-N-cycloalkysulfonylalkanoic amide derivative as in the present invention has not yet been known.

SUMMARY OF THE INVENTION

An object of the present invention is to provide a novel 3-alkoxy-N-cycloalkylsulfonylalkanoic amide derivative useful as a herbicide and a process for preparing the same.

The present inventors have studied intensively in order to solve the above problems, and consequently found that a novel 3-alkoxy-N-cycloalkylsulfonylalkanoic amide derivative shows more excellent herbicidal effect on annual broad-leaved weeds and shows selectivity to crops such as cotton and soy bean, and also found a process for preparing the same with high yields, to accomplish the present invention.

That is, the first invention is concerned to a 3-alkoxy-N-cyclolalkylsulfonylalkanoic amide derivative represented by the formula (I):

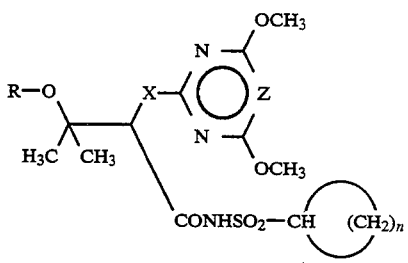

wherein R represents a lower alkyl group, a lower alkenyl group, a lower alkynyl group, a halo-lower alkyl group or a cyano-lower alkyl group; X represents an oxygen atom or a sulfur atom; Z represents a —CH═ group or a nitrogen atom; and n represents an integer of 2 to 9.

The second invention is concerned to a process for preparing the 3-alkoxy-N-cycloalkylsulfonylalkanoic amide derirative represented by the above formula (I), which comprises reacting a compound represented by the formula (II):

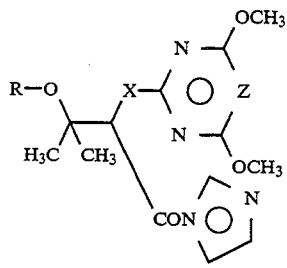

wherein R, X and Z have the same meanings as defined above,
with a compound represented by the formula (III):

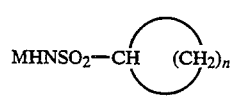

wherein n has the same meaning as defined above; and M represents an alkali metal.

The third invention is concerned to a herbicide comprising the 3-alkoxy-N-cycloalkylsulfonylalkanoic amide derivative represented by the above formula (I) as an active ingredient.

In addition to Preparation method 1 described as the second invention, the following Preparation method 2 may be mentioned as a preferred embodiment for preparing the 3-alkoxy-N-cycloalkylsulfonylalkanoic amide derivative represented by the above formula (I).

Preparation method 2 is concerned to a process for preparing the 3-alkoxy-N-cycloalkylsulfonylalkanoic amide derivative represented by the above formula (I') wherein X is an oxygen atom in the formula (I), which comprises reacting a compound represented by the formula (IV):

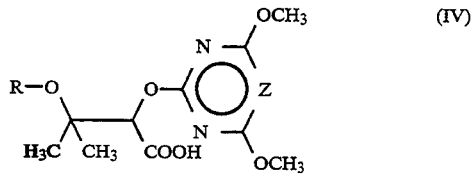

wherein R and Z have the same meanings as defined above,
with a compound represented by the formula (V):

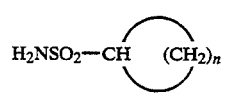

wherein n has the same meaning as defined above.

DESCRIPTION OF THE PREFERRED EMBODIMENTS

In the following, the present invention is explained in detail.

In the novel 3-alkoxy-N-cycloalkylsulfonylalkanoic amide derivative (compound (I)) which is the above desired compound and starting materials thereof (compound (II) to compound (V)), the symbols (R, X, Z, n and M) used therein are as described below.

As R, there may be mentioned a lower alkyl group, a lower alkenyl group, a lower alkynyl group, a halo-lower alkyl group and a cyano-lower alkyl group.

The lower alkyl group represented by R is preferably a straight or branched alkyl group having 1 to 6 carbon atoms, more preferably those having 1 to 4 carbon atoms, particularly preferably those having 1 to 3 carbon atoms (e.g. a methyl group, an ethyl group, an n-propyl group and an isopropyl group).

The lower alkenyl group represented by R is preferably a straight or branched alkenyl group having 2 to 6 carbon atoms, more preferably those having 2 to 4 carbon atoms, particularly preferably a propenyl group (e.g. an allyl group).

The lower alkynyl group represented by R is preferably a straight or branched alkynyl group having 2 to 6 carbon atoms, more preferably those having 2 to 4 carbon atoms, particularly preferably a propynyl group (e.g. a propargyl group).

As the halo-lower alkyl group represented by R, there may be mentioned a straight or branched haloalkyl group having 1 to 6 carbon atoms, preferably those having 1 to 4 carbon atoms, more preferably those having 1 or 2 carbon atoms. As the halogen atom, there may be mentioned a fluorine atom, a chlorine atom, a bromine atom and an iodine atom, preferably a fluorine atom and a chlorine atom. As the most preferred halo-lower alkyl group, there may be mentioned, for example, a fluoroethyl group and a chloroethyl group.

As the cyano-lower alkyl group represented by R, there may be mentioned a straight or branched cyanoalkyl group having 1 to 6 carbon atoms, preferably those having 1 to 4 carbon atoms, more preferably those having 1 to 3 carbon atoms (e.g. a 2-cyanoethyl group).

As X, there may be mentioned an oxygen atom and a sulfur atom.

As Z, there may be mentioned —CH= (a methyn group) and a nitrogen atom.

As n, there may be mentioned an integer of 2 to 9, preferably 2 to 6, more preferably 2 to 4.

As M, there may be mentioned sodium and potassium.

The novel 3-alkoxy-N-cycloalkylsulfonylalkanoic amide derivative (compound (I)) which is a desired compound may include an optical isomer based on an asymmetric carbon atom.

The compound (I) can be prepared by, for example, Preparation method 1 or 2 shown below.

(Preparation method 1)

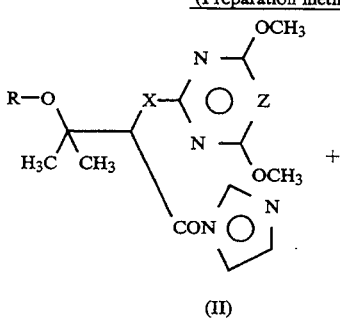

(II)

-continued
(Preparation method 1)

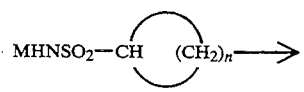

(III)

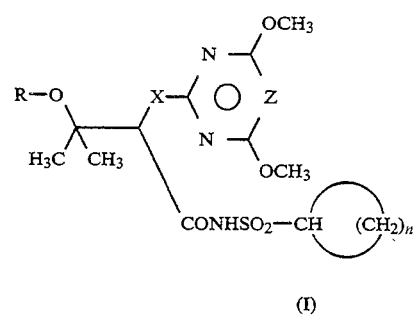

(I)

wherein R, X, Z, n and M have the same meanings as defined above.

The compound (I) can be prepared generally by reacting the compound (II) with the compound (III) in a solvent.

The compound (II) can be prepared by reacting a corresponding carboxylic acid with a commercially available N,N-carbonyldiimidazole in a solvent such as N,N-dimethylformamide (DMF), methylene chloride, benzene and toluene.

As the compound (II), there may be mentioned, for example, the respective compounds (II) (referred to as Compounds (II)$_1$ to (II)$_{32}$) comprising the respective kinds of substituents corresponding to Compounds 1 to 32 shown in Table 1 (for example, Compound (II)$_1$ means a compound wherein R is CH$_3$, X is an oxygen atom and Z is CH in the compound (II)).

The compound (III) can be prepared by reacting sulfonyl chloride prepared according to the method described in "New Experiment Chemistry Lecture", vol. III, p 1790, with ammonia, and reacting the resulting sulfonamide with an alkaline aqueous solution (or an alkali metal alkoxide).

As the compound (III), there may be mentioned, for example, the respective compounds (III) (referred to as Compounds (III)$_1$ to (III)$_{32}$) comprising the respective kinds of substituents corresponding to Compounds 1 to 32 shown in Table 1 (for example, Compound (III)$_1$ means a compound wherein n is 2 and M is an alkali metal in the compound (III)).

The solvent to be used in the synthesis of the compound (I) is not particularly limited so long as it does not participate in the present reaction directly, and may include, for example, ethers such as diethyl ether, tetrahydrofuran and dioxane; bipolar aprotic solvents such as N,N-dimethylformamide and dimethyl sulfoxide; nitriles such as acetonitrile; and a mixture of the above solvents.

The reaction for preparing the compound (I) can be carried out at a reaction concentration of the starting materials of 5 to 80%.

In the preparation method, the ratio of using the starting compounds (II) and (III) is 0.5 to 2 tool, preferably 1 to 1.5 mol of the compound (III) per tool of the compound (II).

The reaction temperature is not particularly limited so long as it is a boiling point of the solvent to be used or lower, but the reaction can be carried out generally at −5° to 30° C.

The reaction time varies depending on the above concentration and temperature, but may be generally carried out within 1 to 24 hours.

(Preparation method 2)

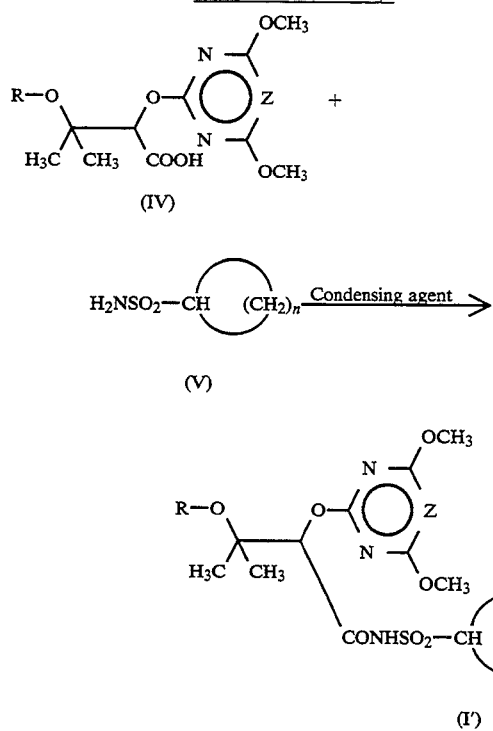

wherein R, Z and n have the same meanings as defined above.

The compound (I) can be prepared generally by reacting the starting compound (IV) with the starting compound (V) in the presence of a condensing agent in a solvent.

The compound (IV) can be prepared by, for example, reacting 3-alkoxy-2-hydroxyalkanoic acid ester and a pyrimidine (or a triazine) in the presence of a base such as sodium hydride and potassium carbonate in a solvent such as acetone, DMF, tetrahydrofuran and acetonitrile, and hydrolyzing the resulting ester, as shown below.

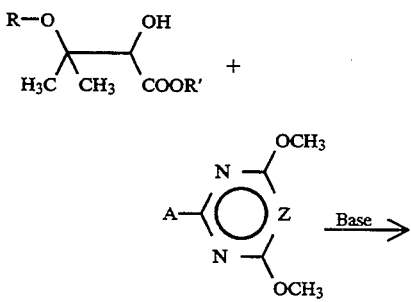

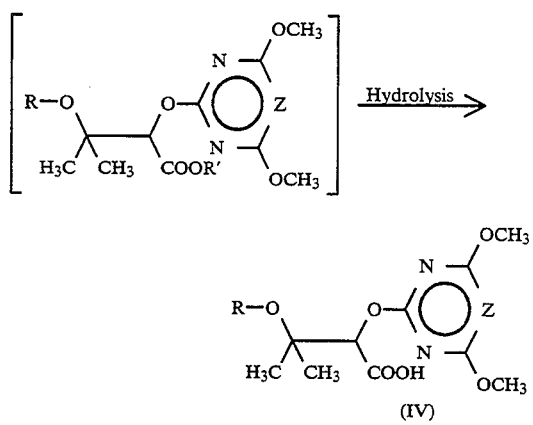

wherein R and Z have the same meanings as defined above; R' represents a lower alkyl group; and A represents a halogen atom or an alkylsulfonyl group having 1 to 6 carbon atoms.

As the compound (IV), there may be mentioned, for example, the respective compounds (IV) (referred to as Compounds $(IV)_1$, $(IV)_2$, $(IV)_5$, $(IV)_8$, $(IV)_{11}$, $(IV)_{14}$, $(IV)_{17}$, $(IV)_{22}$ to $(IV)_{24}$ and $(IV)_{27}$ to $(IV)_{32}$, respectively) comprising the respective kinds of substituents corresponding to Compounds 1, 2, 5, 8, 11, 14, 17, 22 to 24 and 27 to 32 shown in Table 1 (for example, Compound $(IV)_1$ means a compound wherein R is $CH_3$ and Z is CH in the compound (IV)).

The compound (V) can be prepared by reacting sulfonyl chloride prepared according to the method described in "New Experiment Chemistry Lecture", vol. III, p. 1790, with ammonia.

As the compound (V), there may be mentioned, for example, the respective compounds (V) (referred to as Compounds $(V)_1$, $(V)_2$, $(V)_5$, $(V)_8$, $(V)_{11}$, $(V)_{14}$, $(V)_{17}$, $(V)_{22}$ to $(V)_{24}$ and $(V)_{27}$ to $(V)_{32}$, respectively) comprising the respective kinds of substituents corresponding to Compounds 1, 2, 5, 8, 11, 14, 17, 22 to 24 and 27 to 32 shown in Table 1 (for example, Compound $(V)_1$ means a compound wherein n is 2 in the compound (V)).

As the condensing agent, there may be mentioned dicyclohexylcarbodiimide (DCC) and 1-ethyl-3-(3-dimethylaminopropyl)carbodiimide hydrochloride (WSC; trade name, produced by Dojin Kagaku Kenkyusho).

The solvent to be used in the synthesis of the compound (I) is not particularly limited so long as it does not participate in the present reaction directly, and may include, for example, ethers such as ethyl ether, tetrahydrofuran and dioxane; unsubstituted or substituted aromatic hydrocarbons such as benzene, toluene and xylene; halogenated hydrocarbons such as methylene chloride and chloroform; bipolar aprotic solvents such as N,N-dimethylformamide and dimethyl sulfoxide; nitriles such as acetonitrile; and a mixture of the above solvents.

The reaction for preparing the compound (I) can be carried out at a reaction concentration of the starting materials of 5 to 80%.

In the preparation method, the ratio of using the compound (IV) and the compound (V) is 0.5 to 2 mol, preferably 1 to 1.5 mol of the compound (V) per mol of the compound (IV).

The reaction temperature is not particularly limited so long as it is a boiling point of the solvent to be used or lower, but the reaction can be carried out generally at 0° to 50° C.

The reaction time varies depending on the above concentration and temperature, but may be generally carried out within 1 to 24 hours.

As the compound (I) prepared by Preparation method 1 or 2, there may be mentioned, for example, Compounds 1 to 32 shown in Table 1 (for example, Compound 1 means a compound wherein R is $CH_3$, X is an oxygen atom, Z is CH and n is 2 in the compound (I)).

The herbicide containing the compound (I) as an active ingredient has high selectivity to cotton, soy bean and others and also shows excellent herbicidal effect.

That is, the herbicide of the present invention shows excellent herbicidal effect on annual weeds and perennial weeds grown in paddy fields and upland fields, and its herbicidal effect is particularly remarkable in annual grass weeds (e.g. crabgrass (manna-grass), barnyardgrass and foxtail (green panicum)), annual broad-leaved weeds (e.g. morning glory, common lambsquarter (white goosefoot), livid amaranthus, velvetleaf and cocklebur) and perennial weeds (e.g. Johnson grass, bulrush and flatstage).

The herbicide of the present invention shows excellent herbicidal effect on the weeds as described above, but does not give chemical damage on field crops (e.g. cotton and soy bean) at a concentration for such a treatment.

The herbicide of the present invention contains one or more compounds (I) as an active ingredient(s).

The compound (I) can be used singly, but may be preferably used by mixing with a carrier, a surfactant, a dispersant and/or an auxiliary (for example, prepared as a composition such as a dust, an emulsion, a fine granule, a granule, a wettable powder, an oily suspension and an aerosol) according to a conventional method.

As the carrier, there may be mentioned, for example, a solid carrier such as talc, mica, bentonite, clay, kaolin, diatomaceous earth, white carbon, vermiculite, dolomite, zeolite, slaked lime, siliceous sand, silicic anhydride, ammonium sulfate, urea, wood powder, starch and cellulose; a liquid carrier such as hydrocarbons (e.g. kerosine and mineral oil), aromatic hydrocarbons (e.g. benzene, toluene and xylene), chlorinated hydrocarbons (e.g. chloroform and carbon tetrachloride), ethers (e.g. dioxane and tetrahydrofuran) ketones (e.g. acetone, cyclohexanone and isophorone), esters (e.g. ethyl acetate, ethylene glycol acetate and dibutyl maleate), alcohols (e.g. methanol, n-hexanol and ethylene glycol), polar solvents (e.g. dimethylformamide and dimethylsulfoxide) and water; and a gas carrier such as air, nitrogen, carbon dioxide and freon (in the case of a gas carrier, mixed spray can be carried out).

As the surfactant which can be used for improving attachment of the present herbicide to and absorption thereof in plants, and improving characteristics such as dispersion, emulsification and spreading of the herbicide, there may be mentioned nonionic, anionic, cationic or amphoteric surfactants (e.g. alcohol sulfates, alkylsulfonates, lignosulfonates and polyoxyethylene glycol ethers). Further, for improving properties of preparation, carboxymethyl cellulose, polyethylene glycol or gum arabic can be used as an auxiliary.

In preparation of the present herbicide, in addition to the above carrier, surfactant, dispersant and auxiliary, other agricultural chemicals (a fungicide and an insecticide), a fertilizer and a soil conditioner can be used singly or in a suitable combination, respectively, depending on the respective purposes.

When the compound (I) of the present invention is made into preparations, the concentration of the active ingredient is generally 1 to 50% by weight in an emulsion, generally 0.3 to 25% by weight in a dust, generally 1 to 90% by weight in a wettable powder, generally 0.5 to 5% by weight in a granule, generally 0.5 to 5% by weight in an oily dispersion, and generally 0.1 to 5% by weight in an aerosol.

These preparations can be provided for various uses by diluting them to have a suitable concentration and spraying them to stems and/or leaves of plants, soil and paddy field surface, or by applying them directly thereto, depending on the respective purposes.

EXAMPLES

The present invention is described in detail by referring to Examples, but the scope of the present invention is not limited by these Examples.

EXAMPLE 1

(1) Synthesis of N-cyclopropylsulfonyl-2-(4,6-dimethoxypyrimidin-2-yl)thio-3-methoxy-3-methylbutanoic amide (Compound 3).

The compound (I) was synthesized according to the method described in Preparation method 1.

That is, in 10 ml of N,N-dimethylformamide (DMF) was suspended 1.43 g (0.01 mol) of sodium cyclopropylsulfonamide, and 3.52 g (0.01 mol) of 1-[2-(4,6-dimethoxypyrimidin-2-yl)thio-3-methoxy-3-methylbutyl]imidazole dissolved in 10 ml of DMF was added dropwise to the suspension at 0° C. After completion of the dropwise addition, the mixture was stirred at 0° C. for 2 hours and then stirred at 20° C. for 3 hours.

To the reaction mixture was added 30 ml of a saturated citric acid aqueous solution, and the mixture was extracted with ethyl acetate. The ethyl acetate layer was washed with a saturated saline solution and dried over sodium sulfate, and ethyl acetate was removed under reduced pressure. The resulting residue was isolated by column chromatography (Ms gel D-150-60A, trade name, manufactured by Dokai Kagaku Kogyo Co., eluted by n-hexane:ethyl acetate:methanol=1:1:0.05) to obtain 2.83 g (yield: 70%) of the title compound as white crystals.

(2) Synthesis of N-cyclopropylsulfonyl-2-(4,6-dimethoxypyrimidin-2-yl)oxy-3-methoxy-3-methylbutanoic amide (Compound 1).

The compound (I) was synthesized according to the method described in Preparation method 2.

That is, to 20 ml of methylene chloride were added 1.21 g (0.01 mol) of cyclopropylsulfonamide and 2.86 g (0.01 mol) of 2-(4,6-dimethoxypyrimidin-2-yl)oxy-3-methoxy-3-methylbutanoic acid. To the mixture was further added 1.91 g (0.01 mol) of 1-ethyl-3-(3-dimethylaminopropyl)carbodiimide hydrochloride (WSC, trade name, produced by Dojin Kagaku Kenkyusho), and the mixture was stirred at 20° C. for 2 hours.

The reaction mixture was washed with water and dried over sodium sulfate, and methylene chloride was removed under reduced pressure. The resulting residue was isolated by column chromatography (Wako gel C-200, (trade name, manufactured by Wako Junyaku K.K.), eluted by toluene:ethyl acetate=4:1) to obtain 2.92 g (yield: 75%) of the title compound as white crystals.

(3) Syntheses of other compounds (I) in Table 1

In the same manner as in either of the synthetic methods described above, the title compounds (I) as shown in Table 1 were obtained.

TABLE 1

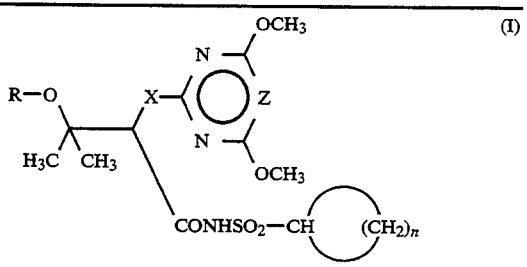

| Compound | R | X | Z | n | Physical property |
|---|---|---|---|---|---|
| 1 | CH$_3$ | O | CH | 2 | m.p. 133 to 135° C. |
| 2 | CH$_3$ | O | N | 2 | |
| 3 | CH$_3$ | S | CH | 2 | m.p. 118 to 120° C. |
| 4 | CH$_3$ | S | N | 2 | m.p. 109 to 111° C. |
| 5 | CH$_3$ | O | CH | 3 | m.p. 98 to 101° C. |
| 6 | CH$_3$ | S | CH | 3 | m.p. 101 to 103° C. |
| 7 | CH$_3$ | S | N | 3 | Oily product |
| 8 | CH$_3$ | O | CH | 4 | |
| 9 | CH$_3$ | S | CH | 4 | $n_D^{24.0}$ 1.5346 |
| 10 | CH$_3$ | S | N | 4 | $n_D^{24.6}$ 1.5350 |
| 11 | C$_2$H$_5$ | O | CH | 2 | m.p. 128 to 130° C. |
| 12 | C$_2$H$_5$ | S | CH | 2 | m.p. 93 to 97° C. |
| 13 | C$_2$H$_5$ | S | N | 2 | $n_D^{20.9}$ 1.5185 |
| 14 | C$_2$H$_5$ | O | CH | 3 | m.p. 119 to 121° C. |
| 15 | C$_2$H$_5$ | S | CH | 3 | |
| 16 | C$_2$H$_5$ | S | N | 3 | |
| 17 | n-C$_3$H$_7$ | O | CH | 2 | m.p. 105 to 106° C. |
| 18 | n-C$_3$H$_7$ | S | CH | 2 | $n_D^{17.7}$ 1.5360 |
| 19 | n-C$_3$H$_7$ | S | N | 2 | $n_D^{17.7}$ 1.5220 |
| 20 | n-C$_3$H$_7$ | S | CH | 3 | |
| 21 | n-C$_3$H$_7$ | S | N | 3 | |
| 22 | CH$_2$=CH—CH$_2$— | O | CH | 2 | |
| 23 | CH$_2$=CH—CH$_2$— | O | CH | 3 | |
| 24 | CH≡C—CH$_2$— | O | CH | 2 | Oily product |
| 25 | CH≡C—CH$_2$— | S | N | 2 | |
| 26 | CH≡C—CH$_2$— | S | N | 3 | |
| 27 | ClCH$_2$CH$_2$— | O | CH | 2 | |
| 28 | FCH$_2$CH$_2$— | O | CH | 2 | m.p. 121 to 123° C. |
| 29 | FCH$_2$CH$_2$— | O | CH | 3 | m.p. 98 to 100° C. |
| 30 | FCH$_2$CH$_2$— | O | CH | 4 | m.p. 97 to 99° C. |
| 31 | CNCH$_2$CH$_2$— | O | CH | 2 | m.p. 132 to 133° C. |
| 32 | CNCH$_2$CH$_2$— | O | CH | 3 | m.p. 131 to 133° C. |

Of these compounds, Compounds No. 1, 3 and 30 are particularly preferred.

EXAMPLE 2

(1) Preparation of granule

Eight (8) parts by weight of Compound 1 was uniformly mixed with 30 parts by weight of bentonite, 59 parts by weight of talc, 1 part by weight of Neopelex powder (trade name, produced by Kao K.K. ) and 2 parts by weight of sodium lignosulfonate, and then the mixture was kneaded with addition of a small amount of water, followed by granulation and drying, to obtain a granule.

(2) Preparation of wettable powder

Fifty (50) parts by weight of Compound 3 was uniformly mixed with 46 parts by weight of kaolin, 2 parts by weight of Neopelex powder (trade name, produced by Kao K.K.) and 2 parts by weight of Demol N (trade name, produced by Kao K.K.), and then the mixture was pulverized to obtain a wettable powder.

(3) Preparation of emulsion

Thirty (30) parts by weight of Compound 4 was added to 60 parts by weight of xylene, 5 parts by weight of dimethylformamide and 5 parts by weight of Sorpol 3005X (trade name, produced by Toho Kagaku Kogyo) and the mixture was uniformly mixed and dissolved to obtain an emulsion.

(4) Preparation of dust

Five (5) parts by weight of Compound 5 was uniformly mixed with 50 parts by weight of talc and 45 parts by weight of clay to obtain a dust.

EXAMPLE 3

(1) Herbicidal test for paddy field

Wagner pots, each having an area of 1/5000 are, were packed with Ube soil (alluvial soil) and planted with seeds or tubers of weeds (barnyardgrass, bulrush and flatstage). Then, the pots were filled with water to a depth of 3 cm.

Each wettable powder of the desired compounds (I) shown in Table 1 prepared in accordance with Example 2 was diluted with water and subjected to dropwise addition treatment by using pipet so that an effective concentration of the compound (I) in each herbicide became 20 g/are at 1 leaf stage of barnyardgrass. These plants were controlled in a glass house at an average temperature of 25° C. for 3 weeks, and then herbicidal effects thereof were investigated.

The herbicidal effects were evaluated according to the 6 ranks (0: None (normal development), 1: Less damaged, 2: Slightly damaged, 3: Moderately damaged, 4: Severely damaged and 5: All killed) as compared with a non-treated district.

The results are shown in Table 2.

TABLE 2

| Compound | Kind of weed | | |
|---|---|---|---|
| | Barnyardgrass | Bulrush | Flatstage |
| 3 | 5 | 5 | 5 |
| 4 | 5 | 4 | 4 |
| 6 | 5 | 4 | 5 |
| 9 | 5 | 5 | 4 |
| 12 | 5 | 5 | 5 |
| 18 | 5 | 5 | 5 |

(2) Soil treatment test for upland field

Wagner pots, each having an area of 1/5000 are, were packed with Ube soil (alluvial soil), and then each seed of cotton, soy bean, crabgrass, barnyardgrass, velvetleaf, common lambsquarter, livid amaranthus, morning glory and cocklebur were planted and covered with soil.

Each wettable powder of the desired compounds (I) shown in Table 1 prepared in accordance with Example 2 was diluted with water and uniformly sprayed on the surface of each soil so that an effective concentration of the compound (I) in each herbicide became 20 g/are. These plants were controlled in a glass house at an average temperature of 25° C. for 3 weeks, and then herbicidal effects thereof were investigated.

The herbicidal effects were evaluated according to the evaluation method described in (1) herbicidal test for paddy field, and the results are shown in Table 3.

TABLE 3

| Compound | Crop Cotton | Crop Soy bean | Crab-grass | Barnyard-grass | Velvet-leaf | Common lambsquarter | Livid amaranthus | Morning glory | Cocklebur |
|---|---|---|---|---|---|---|---|---|---|
| 1 | 0 | 0 | 3 | 3 | 5 | 4 | 3 | 4 | 5 |
| 3 | 0 | 2 | 5 | 5 | 5 | 5 | 5 | 5 | 5 |
| 4 | 0 | 3 | 5 | 5 | 5 | 5 | 5 | 5 | 5 |
| 7 | 0 | 1 | 5 | 4 | 5 | 4 | 5 | 5 | 5 |
| 11 | 0 | 2 | 3 | 3 | 5 | 4 | 3 | 4 | 4 |
| 12 | 0 | 0 | 4 | 5 | 5 | 4 | 4 | 4 | 3 |
| 13 | 0 | 0 | 3 | 3 | 5 | 3 | 3 | 4 | 4 |
| 28 | 1 | 0 | 3 | 3 | 5 | 5 | 5 | 5 | 5 |
| 31 | 0 | 2 | 3 | 3 | 4 | 4 | 3 | 5 | 3 |

(3) Foliar spread test for upland field

Wagner pots, each having an area of 1/5000 are, were packed with volcanic ash soil and then each seed of cotton, soy bean, crabgrass, barnyardgrass, velvetleaf, common lambsquarter, livid amaranthus, morning glory and cocklebur was planted, covered with soil and grown for 2 weeks.

Each wettable powder of the desired compounds (I) shown in Table 1 prepared in accordance with Example 2 was diluted to 2000 ppm with water containing a spreading agent Neoesterin (trade name, produced by Kumiai Kagaku Co.) (500 ppm) and then uniformly sprayed on the above respective plants. After these plants were controlled in a glass house at an average temperature of 25° C. for 3 weeks, the herbicidal effects thereof were investigated.

The herbicidal effects were evaluated according to the evaluation method described in (1) herbicidal test for paddy field, and the results are shown in Table 4.

TABLE 4

| Compound | Crop Cotton | Crop Soy bean | Crab-grass | Barnyard-grass | Velvet-leaf | Common lambsquarter | Livid amaranthus | Morning glory | Cocklebur |
|---|---|---|---|---|---|---|---|---|---|
| 1 | 0 | 3 | 4 | 4 | 5 | 4 | 4 | 5 | 5 |
| 3 | 1 | 3 | 5 | 5 | 5 | 5 | 5 | 5 | 5 |
| 4 | 2 | 3 | 5 | 5 | 5 | 4 | 5 | 5 | 5 |
| 7 | 1 | 2 | 4 | 4 | 5 | 4 | 4 | 5 | 5 |
| 11 | 0 | 3 | 4 | 4 | 5 | 4 | 4 | 5 | 5 |
| 12 | 1 | 2 | 4 | 4 | 5 | 4 | 4 | 5 | 5 |
| 13 | 2 | 2 | 3 | 3 | 4 | 4 | 4 | 5 | 5 |
| 14 | 2 | 2 | 3 | 3 | 4 | 4 | 4 | 5 | 5 |
| 17 | 0 | 0 | 3 | 3 | 4 | 3 | 3 | 5 | 4 |
| 18 | 0 | 0 | 3 | 3 | 4 | 3 | 3 | 5 | 5 |
| 19 | 0 | 0 | 3 | 3 | 4 | 3 | 3 | 5 | 5 |

As clearly seen from the results shown in Tables 2 to 4, the novel 3-alkoxy-N-cycloalkylsulfonylalkanoic acid derivative of the present invention shows excellent herbicidal effect on annual grass weeds, annual broadleaved weeds and perennial weeds, and also has high selectivity to crops such as cotton and soy bean.

We claim:

1. A 3-alkoxy-N-cycloalkylsulfonylalkanoic amide compound represented by the formula (I):

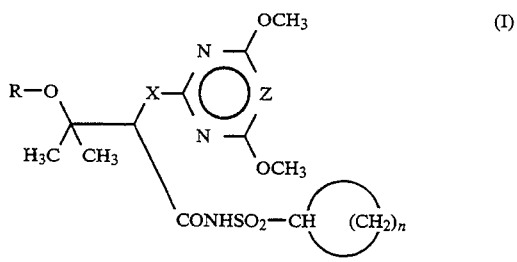

wherein R represents a lower alkyl group, a lower alkenyl group, a lower alkynyl group, a halo-lower alkyl group or a cyano-lower alkyl group; X represents an oxygen atom or a sulfur atom; Z represents a —CH═ group; and n represents an integer of 2 to 9.

2. The compound according to claim 1, wherein R is a straight or branched alkyl group having 1 to 6 carbon atoms, a straight or branched alkenyl group having 2 to 6 carbon atoms, a straight or branched alkynyl group having 2 to 6 carbon atoms, a straight or branched haloalkyl group having 1 to 6 carbon atoms or a straight or branched cyanoalkyl group having 1 to 6 carbon atoms.

3. The compound according to claim 1, wherein R is a straight or branched alkyl group having 1 to 4 carbon atoms, a straight or branched alkenyl group having 2 to 4 carbon atoms, a straight or branched alkynyl group having 2 to 4 carbon atoms, a straight or branched haioalkyl group having 1 to 4 carbon atoms or a straight or branched cyanoalkyl group having 1 to 4 carbon atoms.

4. The compound according to claim 1, wherein R is a straight or branched alkyl group having 1 to 3 carbon atoms, a straight or branched alkenyl group having 2 to 4 carbon atoms, a straight or branched alkynyl group having 2 to 4 carbon atoms, a straight or branched haloalkyl group having 1 or 2 carbon atoms or a straight or branched cyanoalkyl group having 1 to 3 carbon atoms.

5. The compound according to claim 1, wherein R is a methyl group, an ethyl group, an n-propyl group, an isopropyl group, a propenyl group, a propynyl group, a fluoroethyl group, a chloroethyl group or a 2-cyanoethyl group.

6. The compound according to claim 5, wherein n is an integer of 2 to 4.

7. The compound according to claim 6, wherein the compound is at least one selected from the group consisting of:

N-cyclopropylsulfonyl-2-(4,6-dimethoxypyrimidin-2-yl)-oxy-3-methoxy-3-methylbutanoic amide,
N-cyclopropylsulfonyl-2-(4,6-dimethoxypyrimidin-2-yl)-thio-3-methoxy-3-methylbutanoic amide and
N-cyclobutylsulfonyl-2-(4,6-dimethoxypyrimidin-2-yl)-oxy3-(2-fluoroethoxy)-3-methylbutanoic amide.

8. A herbicidal composition comprising an effective amount of a compound represented by the formula (I) according to claim 1 as an active ingredient and a herbicidally effective carrier.

* * * * *

UNITED STATES PATENT AND TRADEMARK OFFICE
CERTIFICATE OF CORRECTION

PATENT NO. : 5,389,601
DATED : February 14, 1995
INVENTOR(S) : Takaaki ABE et al It is certified that error appears in the above-indentified patent and that said Letters Patent is hereby corrected as shown below:

Claim 3, Column 12, Line 60, "haioalkyl" should read --haloalkyl--.

Signed and Sealed this

Twenty-third Day of May, 1995

Attest:

BRUCE LEHMAN

*Attesting Officer*     *Commissioner of Patents and Trademarks*